United States Patent
Nakamura

(10) Patent No.: US 10,024,874 B2
(45) Date of Patent: Jul. 17, 2018

(54) MEASUREMENT-CONTAINER SUPPLY DEVICE

(71) Applicant: JEOL Ltd., Tokyo (JP)

(72) Inventor: Mizuki Nakamura, Tokyo (JP)

(73) Assignee: JEOL Ltd., Tokyo (JP)

( * ) Notice: Subject to any disclaimer, the term of this patent is extended or adjusted under 35 U.S.C. 154(b) by 291 days.

(21) Appl. No.: 14/902,684

(22) PCT Filed: Jun. 20, 2014

(86) PCT No.: PCT/JP2014/066437
§ 371 (c)(1),
(2) Date: Jan. 4, 2016

(87) PCT Pub. No.: WO2015/005101
PCT Pub. Date: Jan. 15, 2015

(65) Prior Publication Data
US 2016/0169925 A1    Jun. 16, 2016

(30) Foreign Application Priority Data
Jul. 8, 2013   (JP) .................................. 2013-142655

(51) Int. Cl.
*G01N 35/04*   (2006.01)
*G01N 35/10*   (2006.01)
(Continued)

(52) U.S. Cl.
CPC ........... *G01N 35/04* (2013.01); *G01N 35/025* (2013.01); *G01N 21/13* (2013.01);
(Continued)

(58) Field of Classification Search
CPC ......... G01N 35/025; G01N 2035/0439; G01N 2035/0441; G01N 2035/0443;
(Continued)

(56) References Cited

U.S. PATENT DOCUMENTS

2007/0269342 A1* 11/2007 Kitagawa ............... G01N 35/04
                                                                              422/64
2012/0171078 A1    7/2012 Kaneko
(Continued)

FOREIGN PATENT DOCUMENTS

EP          1857820 A2    11/2007
JP          8101201 A      4/1996
(Continued)

OTHER PUBLICATIONS

Extended European Search Report re EP 14823305.9 dated Jun. 20, 2016.

*Primary Examiner* — Helen Kwok
*Assistant Examiner* — Nashimiya Fayyaz
(74) *Attorney, Agent, or Firm* — The Webb Law Firm

(57) ABSTRACT

A measurement container supply device. A supply section transfers the measurement container to the predetermined supply position includes a holding section (50) that holds the measurement container, and the holding section (50) has a first groove (52) that is formed to have a width that corresponds to the outer diameter of a body of the measurement container, and a second groove (54) that is formed to have a width that corresponds to the outer diameter of a neck of the measurement container. When the holding section (50) holds the measurement container, the first groove (52) comes in contact with the outer circumferential surface of the body, the second groove (54) comes in contact with the outer circumferential surface of the neck, and a step (56) that is formed by the first groove (52) and the second groove (54) comes in contact with a step that is formed by the body and the neck.

4 Claims, 4 Drawing Sheets

(51) Int. Cl.
*G01N 35/02* (2006.01)
*G01N 21/13* (2006.01)

(52) U.S. Cl.
CPC ........... *G01N 2035/0401* (2013.01); *G01N 2035/0444* (2013.01); *G01N 2035/0462* (2013.01); *G01N 2035/0465* (2013.01)

(58) Field of Classification Search
CPC ... G01N 2035/0444; G01N 2035/0446; G01N 2035/0448; G01N 2035/0449; G01N 2035/0451; G01N 2035/0453; G01N 2035/0455; G01N 2035/0456; G01N 2035/0458; G01N 35/04; G01N 21/13; G01N 2035/0401; G01N 2035/0462; G01N 2035/0465
USPC .............................. 73/863.91, 864.81–864.82
See application file for complete search history.

(56) References Cited

U.S. PATENT DOCUMENTS

2014/0295563 A1* 10/2014 Matsuura ............... G01N 35/04
                                                              436/48
2016/0001981 A1*  1/2016 Nakamura ............. G01N 35/04
                                                              198/443

FOREIGN PATENT DOCUMENTS

| | | |
|---|---|---|
| JP | 2000321197 A | 11/2000 |
| JP | 200127643 A | 1/2001 |
| JP | 2012141226 A | 7/2012 |
| JP | 2013014339 A * | 1/2013 |
| WO | 2009118579 A1 | 10/2009 |

* cited by examiner

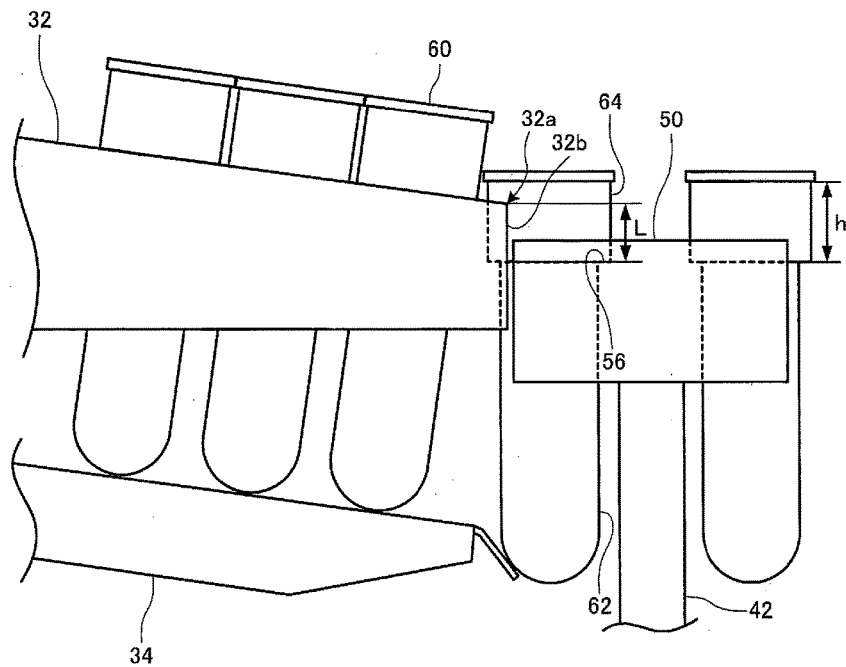
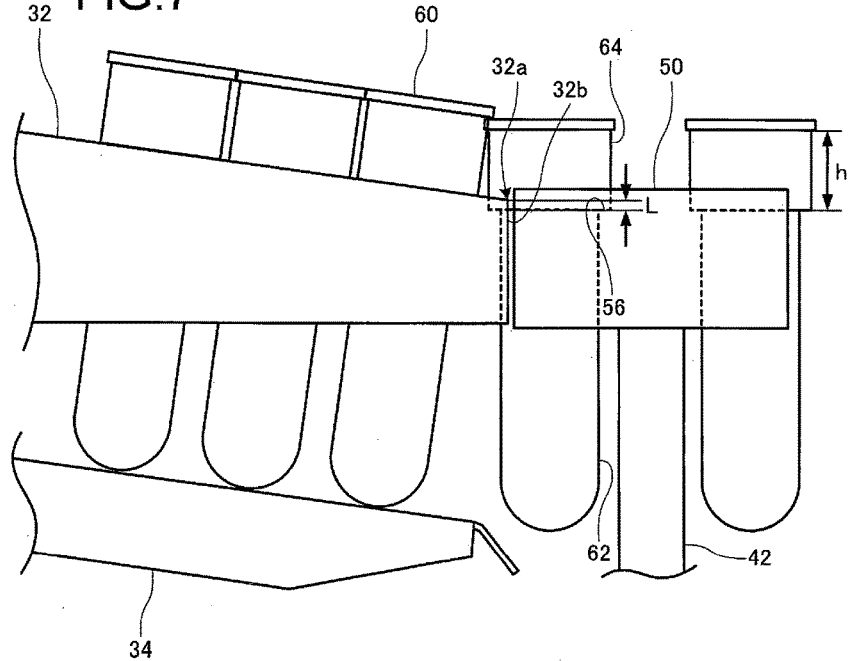

MEASUREMENT-CONTAINER SUPPLY DEVICE

CROSS-REFERENCE TO RELATED APPLICATIONS

This application is the United States national phase of International Application No. PCT/JP2014/066437 filed Jun. 20, 2014, and claims priority to Japanese Patent Application No. 2013-142655 filed Jul. 8, 2013, the disclosures of which are hereby incorporated in their entirety by reference.

TECHNICAL FIELD

The present invention relates to a measurement container supply device that is included in an automatic analyzer.

BACKGROUND ART

A specimen analyzer that includes a container supply device that supplies a container that is used to analyze a specimen is known (see Patent Literature 1, for example). The container supply device includes a storage section that stores a container, a carry-out section that carries the container out of the storage section, a pair of transfer rails that transfer the container carried by the carry-out section, and a rotary transfer section that transfers the container transferred by the pair of transfer rails to a standby position at which a supply catcher section can hold the container. The rotary transfer section includes a rotary table, and the container fitted into a recess formed in the rotary table is transferred to the standby position.

CITATION LIST

Patent Literature

PTL 1: JP-A-2012-141226

SUMMARY OF INVENTION

Technical Problem

Since the above container supply device is configured so that the recess of the rotary table that holds the container has a shape that holds only the body of the container (i.e., a groove-like shape that comes in contact with the outer circumferential surface of the body of the container), it may be difficult to reliably hold the container, and the container may be displaced on the rotary table, or may fall from the rotary table when the rotary table is rotated, for example. As a result, the supply catcher section may not be able to hold the container, and the supply of the container may be delayed.

The invention was conceived in view of the above problems. Several aspects of the invention may provide a measurement container supply device that can more reliably hold a measurement container, and transfer the measurement container to a predetermined supply position.

Solution to Problem (1) According to one aspect of the invention, there is provided a measurement container supply device that is included in an automatic analyzer, the measurement container supply device including:

a storage section that stores a measurement container;

a carry-out section that carries the measurement container out of the storage section;

an alignment transfer section that transfers the measurement container that has been carried by the carry-out section and has aligned along alignment rails toward an end of the alignment rails; and a supply section that holds the measurement container that has been transferred to the end of the alignment rails, and transfers the measurement container to a predetermined supply position, the measurement container including a body, and a neck that has an outer diameter larger than the outer diameter of the body, the supply section including a holding section that holds the measurement container, the holding section having a first groove that is formed to have a width that corresponds to the outer diameter of the body, and a second groove that is formed to have a width that corresponds to the outer diameter of the neck, and when the holding section holds the measurement container, the first groove coming in contact with an outer circumferential surface of the body, the second groove coming in contact with an outer circumferential surface of the neck, and a step that is formed by the first groove and the second groove coming in contact with a step that is formed by the body and the neck.

According to the above measurement container supply device, since the holding section that holds the measurement container has the first groove that is formed to have a width that corresponds to the outer diameter of the body of the measurement container, and comes in contact with the outer circumferential surface of the body, and the second groove that is formed to have a width that corresponds to the outer diameter of the neck of the measurement container, and comes in contact with the outer circumferential surface of the neck, the holding section can hold both the body and the neck of the measurement container. This makes it possible to more reliably hold the measurement container, and suppress displacement or a fall of the measurement container.

(2) In the measurement container supply device, an upper surface of the alignment rails may come in contact with the step that is formed by the body and the neck to support the measurement container in a suspended state, and the holding section may be placed so that the step that is formed by the first groove and the second groove is situated at a position lower than an end upper part of the alignment rails by a predetermined distance.

This makes it possible to suppress displacement or a fall of the measurement container that may occur when only the lower end of the neck of the measurement container held by the holding section comes in contact with the end of the alignment rails.

(3) In the measurement container supply device, the predetermined distance may be equal to or longer than half of the height of the neck.

According to this configuration, since the part of the neck that is situated within a range equal to or greater than half of the height of the neck comes in contact with the end of the alignment rails when the neck of the measurement container held by the holding section comes in contact with the end of the alignment rails, it is possible to suppress displacement or a fall of the measurement container.

(4) In the measurement container supply device, the alignment rails may slope downward toward the end.

BRIEF DESCRIPTION OF DRAWINGS

FIG. 6 is a side view illustrating the configuration of an alignment transfer section and a holding section.

FIG. 7 illustrates a comparative example in which a step of a holding section is situated at a height equivalent to that of the upper surface of the end of an alignment rail.

DESCRIPTION OF EMBODIMENTS

Exemplary embodiments of the invention are described in detail below with reference to the drawings. Note that the following exemplary embodiments do not unduly limit the scope of the invention as stated in the claims. Note also that all of the elements described below should not necessarily be taken as essential elements of the invention.

1. Overall Configuration

Figure 1:
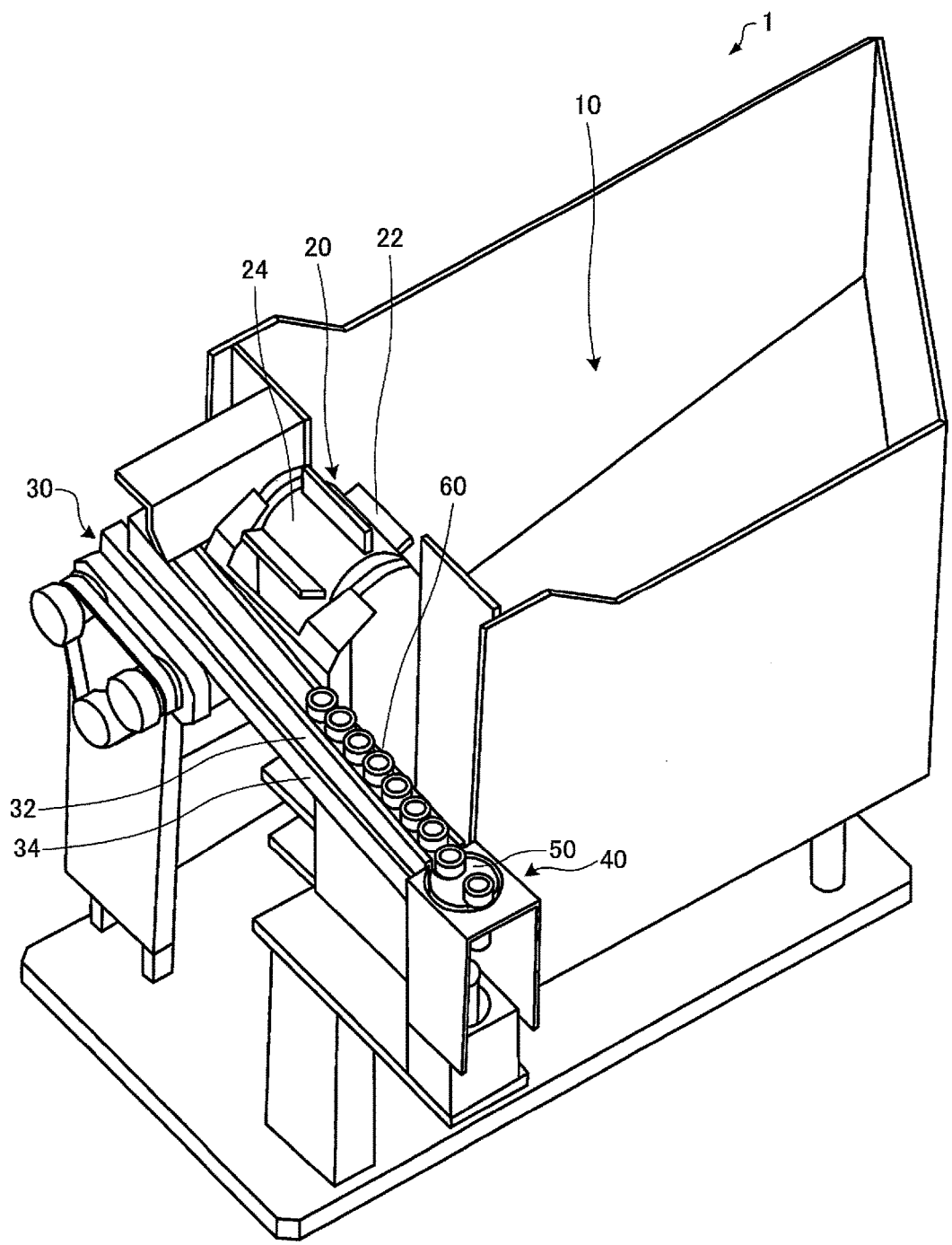
FIG. 1 is a perspective view illustrating an example of the configuration of a measurement container supply device according to one embodiment of the invention.

FIG. 1 illustrates an example of the configuration of a measurement container supply device according to one embodiment of the invention. The measurement container supply device according to one embodiment of the invention is a device that is included in an automatic analyzer (i.e., forms part of the automatic analyzer), and supplies a measurement container that is used to analyze a specimen.

As illustrated in FIG. 1, a measurement container supply device 1 includes a storage section 10 that stores a plurality of measurement containers 60 placed therein, a carry-out section 20 that carries the measurement containers 60 stored in the storage section 10 out of the storage section 10, an alignment transfer section 30 that transfers the measurement containers 60 that have been carried by the carry-out section 20 toward a supply section 40, and the supply section 40 that holds the measurement containers 60 that have been transferred by the alignment transfer section 30, and transfers the measurement container 60 to a predetermined supply position.

The carry-out section 20 includes a belt 24 that is provided with a plurality of holding plates 22 that can hold the measurement container 60, and a driver section that rotates the belt 24. The measurement container 60 stored in the storage section 10 is held by the holding plate 22, transferred upward due to the rotation of the belt 24, and falls from the belt 24 at a position opposite to the storage section 10.

Figure 2:
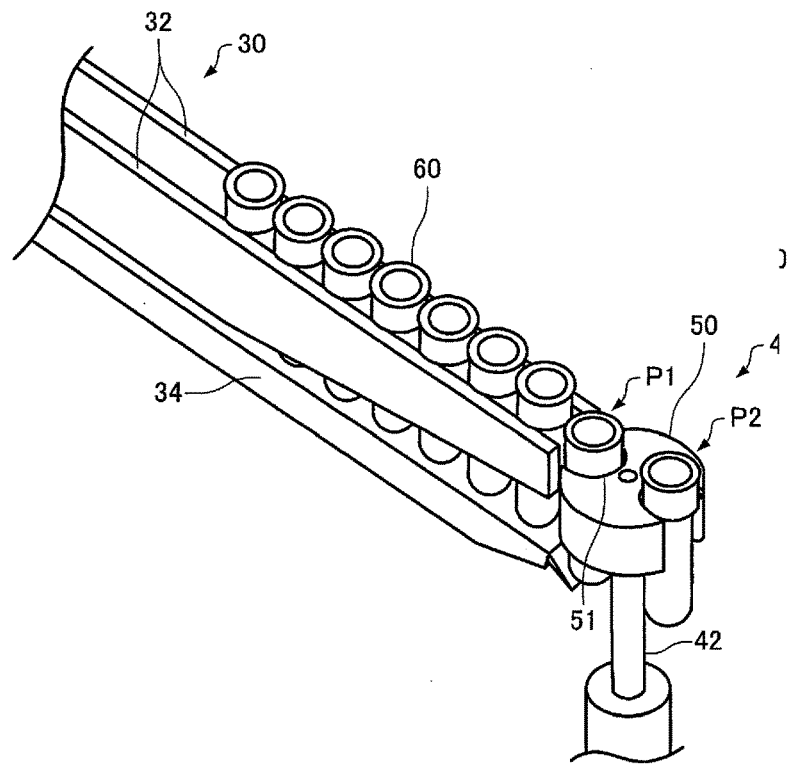
FIG. 2 is a perspective view illustrating the configuration of an alignment transfer section and a supply section.

As illustrated in FIGS. 1 and 2, the alignment transfer section 30 includes a pair of alignment rails 32, an upthrust plate 34 that is provided under the alignment rails 32, and a driver section that causes the upthrust plate 34 to make an upward-downward motion. The alignment rails 32 slope downward toward the end thereof (toward the supply section 40), and the upthrust plate 34 slopes so as to be parallel to the alignment rails 32. The measurement containers 60 that have fallen from the belt 24 align along the alignment rails 32 due to their weight. The measurement containers 60 that have aligned along the alignment rails 32 are transferred toward the end of the alignment rails 32 while making an upward-downward motion due to the upthrust motion of the upthrust plate 34. Note that the measurement containers 60 that have aligned along the alignment rails 32 may be transferred while vibrating the measurement containers 60, or may be transferred using a belt or the like. The measurement containers 60 may be allowed to slide along the alignment rails 32 due to their weight.

The supply section 40 includes a holding section 50 that holds the measurement containers 60, a support section 42 that supports the holding section 50 so as to be rotatable, and a driver section that rotates the holding section 50. The holding section 50 is provided with two holding guides 51 that can respectively hold the measurement container 60. The measurement container 60 that has been transferred to the end of the alignment rails 32 is fitted into the holding guide 51 that is formed at a position P1, and the holding section 50 is rotated by 180° around the vertical axis so that the measurement container 60 is transferred to a supply position P2. The measurement container 60 that has been transferred to the supply position P2 is removed by an external transfer section (e.g., arm), and transferred to another area of the automatic analyzer. A specimen and a reagent are put in the measurement container 60 that has been transferred to the other area of the automatic analyzer. After completion of a predetermined treatment, a specific substance included in the specimen is quantitatively analyzed using an optical means, a magnetic means, or a chemical means.

Note that the alignment rails 32 are provided with a sensor that detects whether or not a predetermined number or more of measurement containers 60 have aligned along the alignment rails 32, and the carry-out section 20 stops operation when it has been detected that a predetermined number or more of measurement containers 60 have aligned along the alignment rails 32. The supply section 40 has a sensor at the supply position P2, and the sensor detects whether or not the measurement container 60 is present at the supply position P2. When it has been detected that the measurement container 60 is not present at the supply position P2, the removal operation of the external transfer section (e.g., arm) is suspended for a given time, and is resumed after the measurement container 60 has been transferred to the supply position P2.

Figure 3:
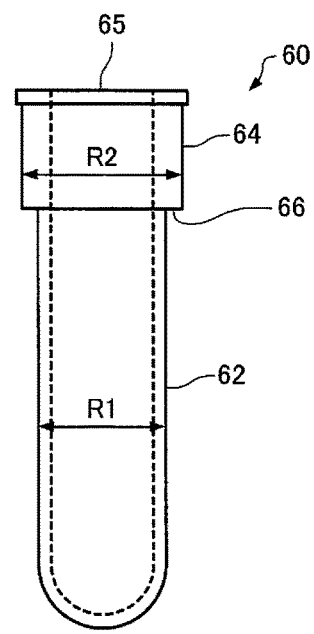
FIG. 3 is a side view illustrating the configuration of a measurement container.

FIG. 3 illustrates an example of the configuration of the measurement container 60. As illustrated in FIG. 3, the measurement container 60 is a container that has an approximately cylindrical shape, and has an upper opening. The measurement container 60 includes a body 62 that has an outer diameter R1, and a neck 64 that has an outer diameter R2 that is larger than the outer diameter R1. An opening 65 of the measurement container 60 is situated over the neck 64. A step 66 is formed at the interface (boundary) between the neck 64 and the body 62. As illustrated in FIG. 2, the alignment rails 32 (that make a pair) are configured so that the upper surface thereof comes in contact with the step 66 of the measurement container 60 to support the measurement container 60 in a suspended state. Specifically, the alignment rails 32 (that make a pair) are disposed in parallel to each other at an interval that is larger than the outer diameter R1 of the body 62 and is smaller than the outer diameter R2 of the neck 64.

2. Configuration of Holding Section

Figure 4:
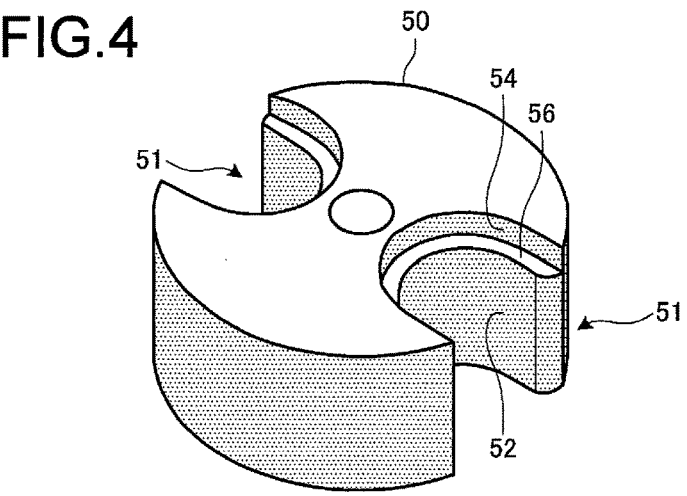
FIG. 4 is a perspective view illustrating the configuration of a holding section.
Figure 5A:
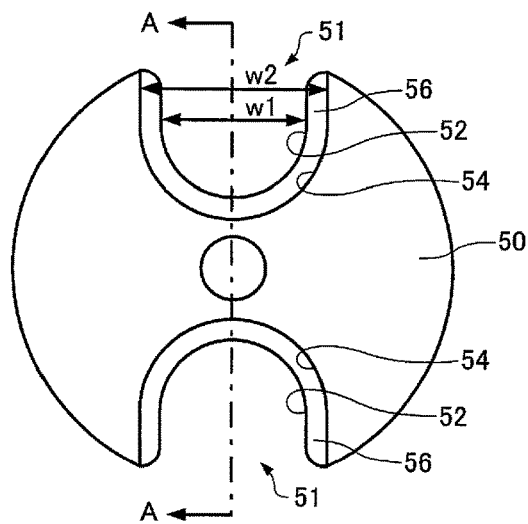
FIG. 5A is a plan view illustrating the configuration of a holding section.
Figure 5B:
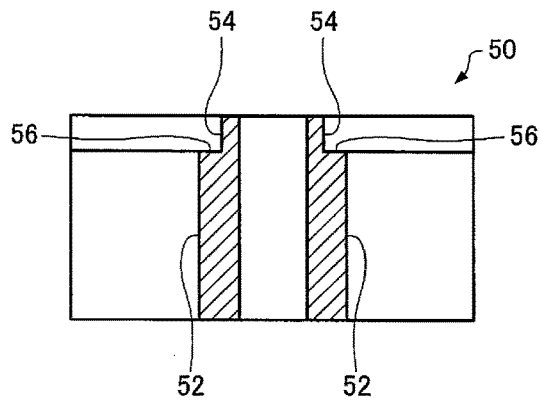
FIG. 5B is a cross-sectional view taken along the line A-A in FIG. 5A.

FIG. 4 is a perspective view illustrating the configuration of the holding section 50, FIG. 5A is a plan view illustrating the configuration of the holding section 50, and FIG. 5B is a cross-sectional view taken along the line A-A illustrated in FIG. 5A.

As illustrated in FIGS. 4, 5A, and 5B, the holding section 50 has a first groove 52 that is formed to have a width w1 that corresponds to the outer diameter R1 of the body 62 of the measurement container 60, and a second groove 54 that is formed to have a width w2 that corresponds to the outer diameter R2 of the neck 64 of the measurement container 60. Note that the width w1 refers to the maximum width of the first groove 52, and is equal to the outer diameter R1, or slightly larger than the outer diameter R1. The width w2 refers to the maximum width of the second groove 54, and is equal to the outer diameter R2, or slightly larger than the outer diameter R2. A step 56 is formed at the interface (boundary) between the first groove 52 and the second groove 54. Each of the holding guides 51 is formed by the first groove 52 and the second groove 54, and holds the measurement container 60 so that the longitudinal direction of the measurement container 60 is parallel to the vertical axis.

When the holding section 50 holds the measurement container 60, the first groove 52 comes in contact with the outer circumferential surface (outer circumferential part) of the body 62, the second groove 54 comes in contact with the outer circumferential surface (outer circumferential part) of the neck 64, and the step 56 comes in contact with the step 66 formed by (between) the body 62 and the neck 64.

Since the measurement container supply device 1 according to one embodiment of the invention has a configuration in which the first groove 52 that guides the body 62 and the second groove 54 that guides the neck 64 are formed in the holding section 50, the holding section 50 can hold both the body 62 and the neck 64 of the measurement container 60. This makes it possible to more reliably hold the measurement container 60, and suppress displacement or a fall of the measurement container 60 during transfer.

FIG. 6 is a side view illustrating the configuration of the alignment transfer section 30 and the holding section 50. As illustrated in FIG. 6, the holding section 50 is placed so that the step 56 is situated at a position lower than an end upper part 32a of the alignment rail 32 by a predetermined distance L. The predetermined distance L is desirably set to be equal to or longer than half of the height h of the neck 64 of the measurement container 60.

The holding section 50 is placed close to the end of the alignment rails 32 in order to hold the measurement container 60 that has been transferred to the end of the alignment rails 32. Therefore, the outer circumferential part (i.e., the part of the outer circumferential part that is situated within the range of the distance L from the lower end of the outer circumferential part) of the neck 64 of the measurement container 60 may come in contact with a side 32b of the end of the alignment rails 32 when the measurement container 60 that is held by the holding section 50 is transferred (rotated).

If the holding section 50 is placed so that the distance L (vertical distance) from the end upper part 32a of the alignment rails 32 to the step 56 is sufficiently short (i.e., the step 56 is situated at a height equivalent to that of the end upper part 32a) (see FIG. 7), only the lower end of the neck 64 may come in contact with the side 32b of the end of the alignment rails 32 (i.e., the measurement container 60 may be tilted) when the measurement container 60 is transferred (rotated), and displacement or a fall of the measurement container 60 may occur.

Therefore, the measurement container supply device 1 according to one embodiment of the invention is configured so that the distance L (vertical distance) from the end upper part 32a of the alignment rails 32 to the step 56 is sufficiently long (see FIG. 6). Specifically, the distance L is set to be equal to or longer than half of the height h of the neck 64. According to this configuration, since most of the outer circumferential part (including the lower end) of the neck 64 (i.e., the part of the neck 64 that is situated within a range equal to or greater than half of the height h of the neck 64) comes in contact with the side 32b of the alignment rails 32 when the outer circumferential part of the neck 64 comes in contact with the side 32b of the alignment rails 32, the measurement container 60 is not tilted, and it is possible to suppress displacement or a fall of the measurement container 60.

The measurement container 60 is supported by the alignment rails 32 in a state in which the measurement container 60 is tilted relative to the vertical axis, and is held by the holding section 50 in a state in which the measurement container 60 is parallel to the vertical axis (i.e., vertically held by the holding section 50). Therefore, when the step 56 is situated at a height equivalent to that of the end upper part 32a (see FIG. 7), the neck 64 of the measurement container 60 that is held by the holding section 50 may come in contact with the neck 64 of another measurement container 60 that is situated at the end of the alignment rails 32 when the measurement container 60 is transferred (rotated). When the holding section 50 is placed so that the step 56 is situated at a position lower than the end upper part 32a by the distance L (see FIG. 6), it is possible to minimize the contact between the necks 64 of the measurement containers 60, and suppress displacement or a fall of the measurement container 60 that is held by the holding section 50.

3. Modifications

The invention is not limited to the above embodiments. Various modifications and variations may be made of the above embodiments. The invention includes configurations that are substantially the same as the configurations described in connection with the above embodiments (e.g., in function, method and effect, or objective and effect). The invention also includes a configuration in which an unsubstantial element described in connection with the above embodiments is replaced by another element. The invention also includes a configuration having the same effects as those of the configurations described in connection with the above embodiments, or a configuration capable of achieving the same object as those of the configurations described in connection with the above embodiments. The invention further includes a configuration obtained by adding known technology to the configurations described in connection with the above embodiments.

Although the above embodiments have been described taking an example in which the holding section 50 has two holding guides 51, the holding section 50 may have only one holding guide 51, or may have three or more holding guides 51.

Although the above embodiments have been described taking an example in which the measurement container 60 is transferred to a predetermined supply position by rotating the holding section 50, the measurement container 60 may be transferred to a predetermined supply position by causing the holding section 50 to make an upward-downward motion or a forward-backward motion.

REFERENCE SIGNS LIST

1: measurement container supply device, 10: storage section, 20: carry-out section, 22: holding plate, 24: belt, 30:

alignment transfer section, 32: alignment rail, 34: upthrust plate, 40: supply section, 42: support section, 50: holding section, 51: holding guide, 52: first groove, 54: second groove, 56: step, 60: measurement container, 62: body, 64: neck, 65: opening, 66: step

The invention claimed is:

1. A measurement container supply device that is included in an automatic analyzer, the measurement container supply device comprising:
  a storage section that stores a measurement container;
  a carry-out section that carries the measurement container out of the storage section;
  an alignment transfer section that transfers the measurement container that has been carried by the carry-out section and has aligned along alignment rails toward an end of the alignment rails; and
  a supply section that holds the measurement container that has been transferred to the end of the alignment rails, and transfers the measurement container to a predetermined supply position,
  the measurement container including a body, and a neck that has an outer diameter larger than the outer diameter of the body,
  the supply section including a holding section that holds the measurement container,
  the holding section having a first groove that is formed to have a width that corresponds to the outer diameter of the body, and a second groove that is formed to have a width that corresponds to the outer diameter of the neck, and
  when the holding section holds the measurement container, the first groove coming in contact with an outer circumferential surface of the body, the second groove coming in contact with an outer circumferential surface of the neck, and a step that is formed by the first groove and the second groove coming in contact with a step that is formed by the body and the neck,
  wherein an upper surface of the alignment rails comes in contact with the step that is formed by the body and the neck to support the measurement container in a suspended state, and
  wherein the holding section is placed so that the step that is formed by the first groove and the second groove is situated at a position lower than an end upper part of the alignment rails by a predetermined distance.

2. The measurement container supply device as defined in claim 1,
  wherein the predetermined distance is equal to or longer than half of the height of the neck.

3. The measurement container supply device as defined in claim 1,
  wherein the alignment rails slope downward toward the end.

4. The measurement container supply device as defined in claim 2,
  wherein the alignment rails slope downward toward the end.

* * * * *